US009775539B2

(12) United States Patent
Carter

(10) Patent No.: US 9,775,539 B2
(45) Date of Patent: Oct. 3, 2017

(54) MEDICAL DEVICE IMPLANTATION IMAGING

(71) Applicant: Paul Michael Carter, West Pennant Hills NSW (AU)

(72) Inventor: Paul Michael Carter, West Pennant Hills NSW (AU)

(73) Assignee: Cochlear Limited, Macquarie University, NSW (AU)

(*) Notice: Subject to any disclaimer, the term of this patent is extended or adjusted under 35 U.S.C. 154(b) by 255 days.

(21) Appl. No.: 13/762,600

(22) Filed: Feb. 8, 2013

(65) Prior Publication Data
US 2014/0228669 A1  Aug. 14, 2014

(51) Int. Cl.
| *A61B 5/05* | (2006.01) |
| *A61B 5/06* | (2006.01) |
| *A61N 1/36* | (2006.01) |
| *A61N 1/05* | (2006.01) |
| *A61B 5/00* | (2006.01) |
| *A61M 25/01* | (2006.01) |
| *A61B 17/00* | (2006.01) |
| *A61B 34/20* | (2016.01) |

(52) U.S. Cl.
CPC .............. *A61B 5/062* (2013.01); *A61B 5/743* (2013.01); *A61N 1/0541* (2013.01); *A61N 1/36032* (2013.01); *A61B 5/686* (2013.01); *A61B 2017/00787* (2013.01); *A61B 2034/2051* (2016.02); *A61M 25/0127* (2013.01)

(58) Field of Classification Search
None
See application file for complete search history.

(56) References Cited

U.S. PATENT DOCUMENTS

| 5,833,608 | A | 11/1998 | Acker | |
| 6,432,041 | B1* | 8/2002 | Taniguchi et al. | ............ 600/117 |
| RE40,852 | E * | 7/2009 | Martinelli et al. | ............ 600/424 |
| 7,818,044 | B2 | 10/2010 | Dukesherer et al. | |
| 2004/0116775 | A1* | 6/2004 | Taniguchi | ................ A61B 5/06 600/117 |
| 2004/0260362 | A1* | 12/2004 | Darley | ..................... A61N 1/08 607/57 |
| 2005/0245811 | A1* | 11/2005 | Scheffler | ....................... 600/410 |

(Continued)

FOREIGN PATENT DOCUMENTS

WO   WO2012/055436   *   5/2012

OTHER PUBLICATIONS

Electronic Instrumentation Laboratory—Research, "Medical Measurement Systems, Magnetic system for intravascular navigation," retrieved from http://wwwetis.et.tudelft.nl/research/descriptions/french_medical.htm, on Dec. 3, 2012, pp. 1-2.

*Primary Examiner* — Amanda Lauritzen Moher
*Assistant Examiner* — Shahdeep Mohammed
(74) *Attorney, Agent, or Firm* — Edell, Shapiro & Finnan, LLC

(57) ABSTRACT

Implantation imaging techniques are presented herein to provide a surgeon with visual feedback during implantation of an implantable medical device in a recipient. The implantation imaging techniques may include the generation of a magnetic field that induces a voltage at a coil positioned in the recipient. The induced voltage is used to determine the orientation of the coil positioned in the recipient relative to direction of the magnetic field.

19 Claims, 14 Drawing Sheets

(56) References Cited

U.S. PATENT DOCUMENTS

| | | | |
|---|---|---|---|
| 2008/0221425 A1* | 9/2008 | Olson et al. | 600/407 |
| 2011/0098719 A1* | 4/2011 | Llinas | A61N 1/0541 606/129 |
| 2011/0160568 A1* | 6/2011 | Seeley et al. | 600/424 |
| 2013/0006044 A1* | 1/2013 | Menzl | H04R 25/606 600/25 |

* cited by examiner

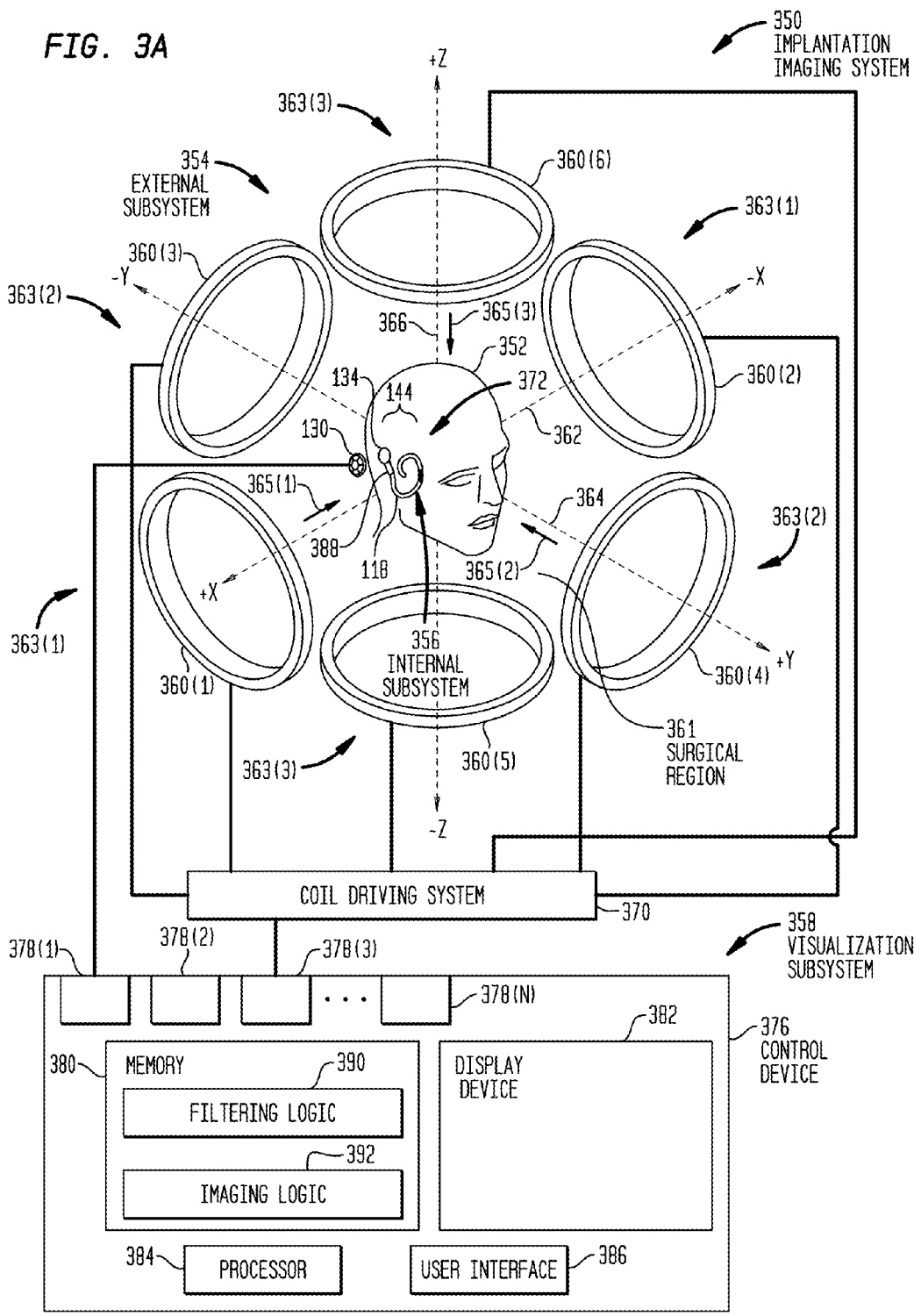

MEDICAL DEVICE IMPLANTATION IMAGING

BACKGROUND

Field of the Invention

The present invention relates generally to implantation of medical devices, and more particularly, to medical device implantation imaging.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing life saving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify the anatomy or of a physiological process.

SUMMARY

In one aspect of the invention, a system is provided. The system comprises a first external coil arranged about a first axis and configured to generate a magnetic field within a surgical region and an elongate assembly configured to be inserted into a recipient located in the surgical region. The elongate assembly comprises an assembly coil configured to detect the magnetic field generated by the first external coil and to generate a voltage for use in determining an orientation of the assembly coil with respect to the first axis.

In another aspect of the present invention, a method is provided. The method comprises inserting an elongate assembly comprising an assembly coil into a recipient located in a surgical region and generating a magnetic field within the surgical region with a first external coil that is arranged about a first axis and positioned in proximity to the surgical region. The method further comprises detecting the magnetic field at the assembly coil such that a voltage is induced at the assembly coil, and determining, based on the induced voltage, an orientation of the assembly coil with respect to the first axis.

BRIEF DESCRIPTION OF THE DRAWINGS

Embodiments of the present invention are described herein in conjunction with the accompanying drawings, in which:

FIG. 3A is schematic diagram of an implantation imaging system in accordance with embodiments of the present invention;

DETAILED DESCRIPTION

There are many different types of implantable medical devices having a wide variety of corresponding implantable components that may be partially or fully implanted into a recipient. For example, implantable medical devices may include hearing prostheses (e.g., auditory brain stimulators, bone conduction devices, mechanical stimulators, cochlear implants, etc.), sensors, implantable pacemakers, defibrillators, functional electrical stimulation devices, catheters, etc.

Embodiments of the present invention are generally directed to implantation imaging techniques for providing a surgeon with visual feedback during implantation of any of the above or other implantable medical device now know or later developed. The implantation imaging techniques may include the generation of a magnetic field that induces a voltage at a coil positioned in the recipient. The induced voltage is used to determine the orientation of the coil positioned in the recipient relative to direction of the magnetic field. For ease of illustration, the implantation imaging techniques are primarily described herein in connection with the implantation of stimulating assembly of a cochlear implant (also commonly referred to as cochlear implant device, cochlear prosthesis, and the like; simply "cochlear implant" herein).

Figure 1:
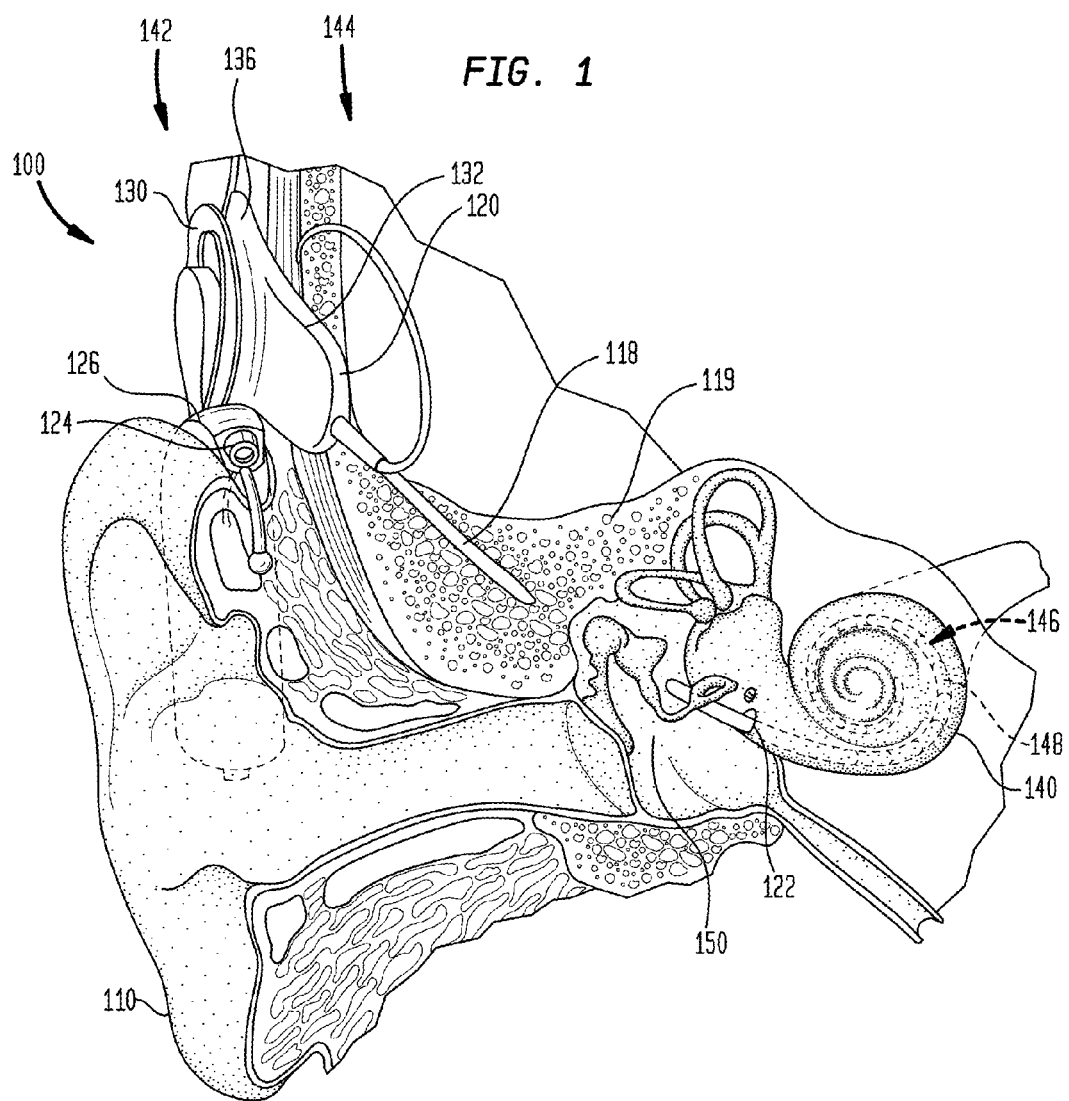
FIG. 1 is a schematic diagram of a cochlear implant having an implantable component implanted in a recipient through the use of an implantation imaging system in accordance with embodiments of the present invention.

FIG. 1 is perspective view of an exemplary cochlear implant 100 that comprises an external component 142 and an internal or implantable component 144. The external component 142 is directly or indirectly attached to the body of the recipient and typically comprises one or more sound input elements 124 (e.g., microphones, telecoils, etc.) for detecting sound, a sound processor 126, a power source (not shown), an external coil 130 and, generally, a magnet (not shown) fixed relative to the external coil 130. The sound processor 126 processes electrical signals generated by a sound input element 124 that is positioned, in the depicted embodiment, by auricle 110 of the recipient. The sound processor 126 provides the processed signals to external coil 130 via a cable (not shown).

The internal component 144 comprises an elongate stimulating assembly 118, a stimulator unit 120, and an internal receiver/transceiver unit 132, sometimes referred to herein as transceiver unit 132. The transceiver unit 132 is connected to an internal coil 136 and, generally, a magnet (not shown) fixed relative to the internal coil 136. Internal transceiver unit 132 and stimulator unit 120 are sometimes collectively referred to herein as a stimulator/transceiver unit.

The magnets in the external component 142 and internal component 144 facilitate the operational alignment of the external coil 130 with the internal coil 136. The operational alignment of the coils enables the internal coil 136 to transmit/receive power and data to/from the external coil 130. More specifically, in certain examples, external coil 130 transmits electrical signals (e.g., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding. In use, transceiver unit 132 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 has a proximal end connected to the stimulator unit 120 and a distal end implanted in cochlea 140. Elongate stimulating assembly 118 also includes a contact array 146 that comprises a plurality of stimulating contacts 148 that may be electrical and/or optical contacts. Stimulating assembly 118 extends from stimulator unit 120 to cochlea 140 through mastoid bone 119 and a cochleostomy 122.

There are a variety of types of intra-cochlear stimulating assemblies that may be inserted into a recipient's cochlea. For example, a perimodiolar stimulating assembly is a stimulating assembly that is configured to adopt a curved configuration during and/or after implantation into the recipient's cochlea. To achieve this, the stimulating assembly may be pre-curved to the same general curvature of a cochlea. Perimodiolar stimulating assemblies are typically held straight by, for example, a stiffening stylet or sheath which is removed during implantation. Varying material combinations or shape memory materials may also be used so that the stimulating assembly may adopt its curved configuration when in the cochlea.

A stimulating assembly can also be a non-perimodiolar stimulating assembly. A non-perimodiolar stimulating assembly may be a substantially straight assembly, a mid-scala assembly which assumes a midscale position during or following implantation, or a short assembly electrode implanted into at least a basal region of the cochlea. The stimulating assembly may extend towards apical end of cochlea, referred to as the cochlea apex.

To insert any of the above or other intra-cochlear stimulating assemblies, such as stimulating assembly 118, an opening (facial recess) is created through the recipient's mastoid bone 119 to access the recipient's middle ear cavity 150. Using this opening, the surgeon drills an opening (the cochleostomy 122) from the middle ear into the cochlea 140 through, for example, the round window, oval window, the promontory or an apical turn of the cochlea 140. The surgeon then gently pushes the stimulating assembly 118 forward into the cochlea 140 until the stimulating assembly achieves a desired position.

In conventional intra-cochlear stimulating assembly insertion techniques, the surgeon typically operates "blind." That is, due to the nature of the access (through the facial recess and the cochleostomy), the surgeon cannot actually see the stimulating assembly once it passes into the cochlea. Therefore, the only feedback about the state of the stimulating assembly during and immediately after the insertion is tactile feedback (i.e., touch/feel of the surgeon).

Figure 2A:
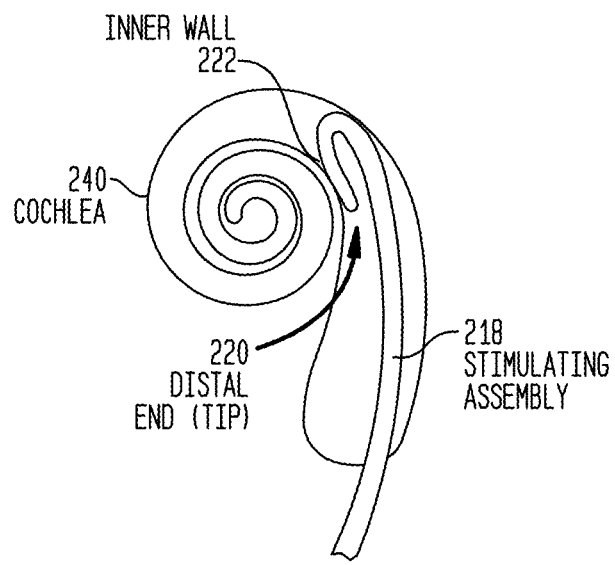
FIGS. 2A and 2B are schematic diagrams illustrating events that may occur during insertion of a stimulating assembly into a recipient's cochlea.
Figure 2B:
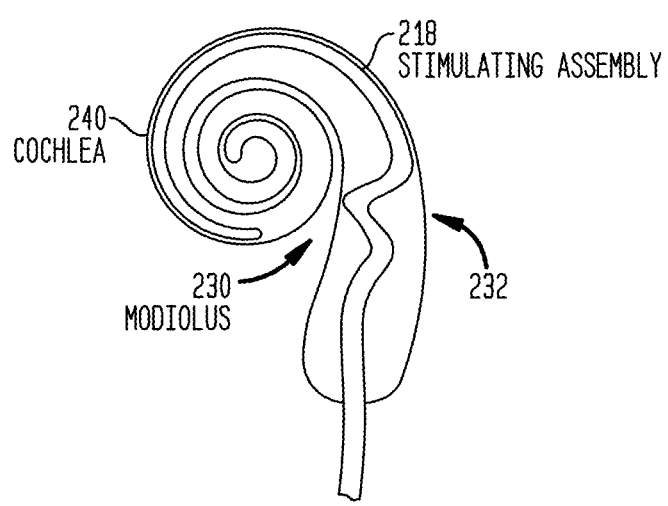

FIGS. 2A and 2B illustrate several events that are possible during insertion of a stimulating assembly 218 into a recipient's cochlea 240 which can negatively impact the placement of the electrode array within the cochlea. More particularly, FIG. 2A illustrates an example where friction and other forces cause the distal end or tip 220 of the stimulating assembly 218 to stick to (i.e., get caught on) inner wall 222 of the cochlea 240. In this example, not only can the surgeon not see that the distal end 220 is caught on the inner wall 222, but he/she also may not feel the resistance provided by the wall. As such, the surgeon may continue to push the stimulating assembly 218 into the cochlea 240 and the stimulating assembly may fold over onto itself. This type of event is generally referred to as tip foldover.

In another insertion event, the distal end 220 of the stimulating assembly 218 may not become caught on the wall of the cochlea 240, but rather may perforate a wall of the cochlea 240. For example, the stimulating assembly 218 may perforate the basilar membrane of the cochlea 240 causing trauma to structures in the cochlea 240.

In a further example, shown in FIG. 2B, the stimulating assembly 218 deforms or buckles at a region 232. This deformation, which cannot be seen by the surgeon, may prevent the stimulating assembly 218 from assuming an optimal placement, such as a position close to the modiolus 230.

Figure 2C:
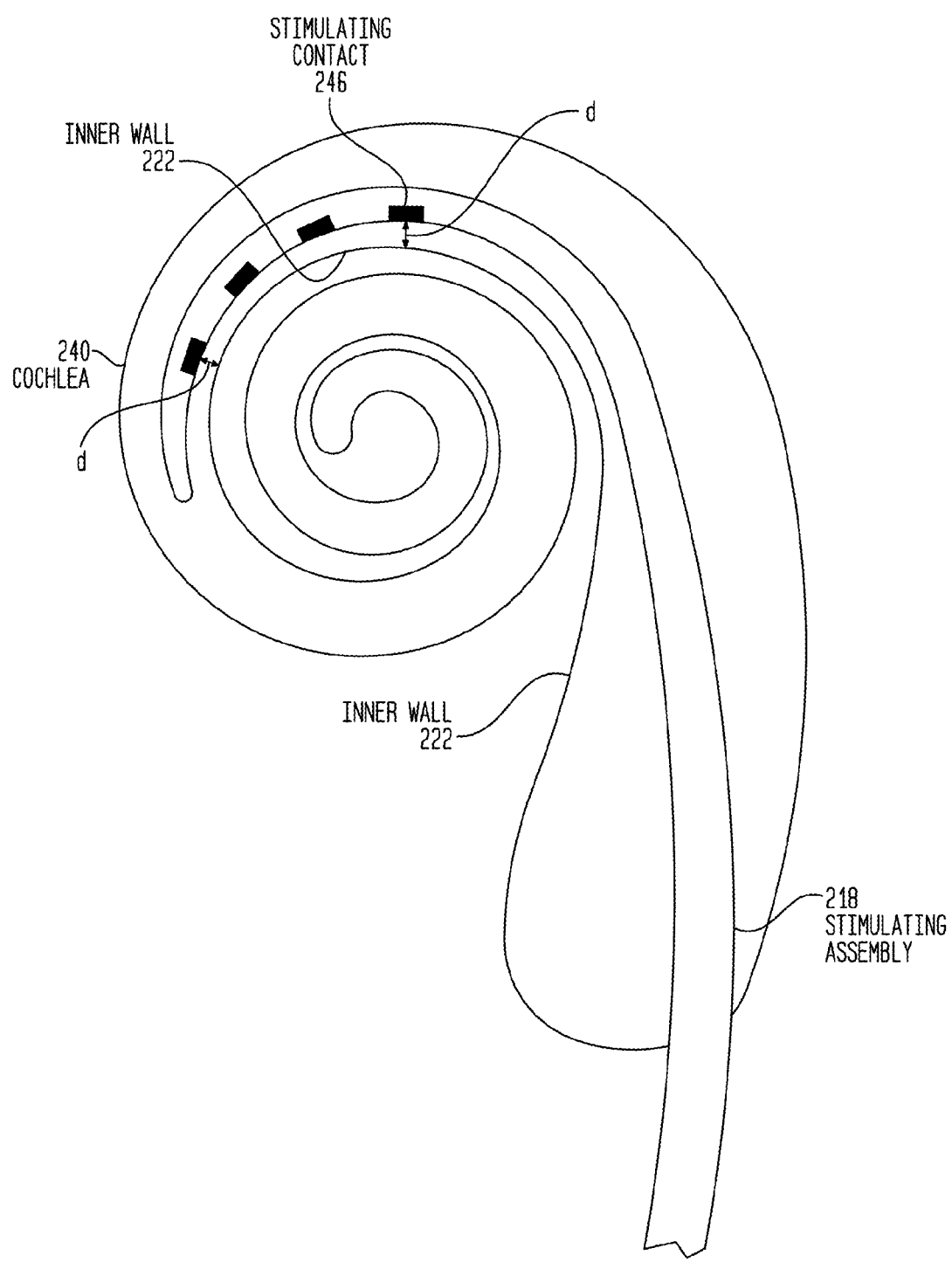
FIG. 2C is a schematic diagram illustrating a mid scalar position of a stimulating assembly within a recipient's cochlea.

For at least perimodiolar electrode designs it is understood that the proximity of the stimulating contacts to target neural elements (e.g., modiolus) is positively correlated with cochlear implant performance. That is, performance of a cochlear implant improves when the stimulating contacts are positioned close to the target neural elements. Therefore, in addition to the events illustrated in FIGS. 2A and 2B, it is also useful for the surgeon to understand the proximity of the stimulating assembly to the inner wall 222 of the cochlea 230. FIG. 2C illustrates an example in which cochlear implant stimulating assembly 218 has stimulating contacts 246 that, when inserted, are separated from the cochlea inner wall 222 by a distance (d). During insertion, the surgeon attempts to minimize the distance (d) to improve the efficiency of the electrical stimulation provided by stimulating contacts 246 in a perimodiolar electrode design.

Each of the above and other insertions events can negatively affect the hearing outcome of the recipient. However, as noted above, the only way for a surgeon to determine that certain events are occurring during conventional insertion techniques is through the use of tactile feedback (i.e., the touch/feel of the surgeon as the surgeon pushes the stimulating assembly into the cochlea). Accordingly, implantation imaging techniques are presented herein that provide the surgeon with visual feedback of the stimulating assembly during insertion into the cochlea. With the assistance of the implantation imaging techniques, a surgeon can determine, in real-time, if an event is occurring and, accordingly, take immediate corrective action. The use of visual or other feedback may minimize the incidence of the above and other events that may arise during the insertion of a stimulation assembly.

FIG. 3A is a schematic diagram illustrating an implantation imaging system 350 in accordance with embodiments of the present invention used to implant stimulating assembly 118 (FIG. 1) into a recipient 352. Implantation imaging system 350 comprises an external subsystem 354, an internal subsystem 356, and a visualization subsystem 358 that collectively operate to provide a surgeon with a real time, three-dimensional information of the stimulating assembly 118 and its position relative to the surrounding structures of cochlea 140.

External subsystem 354 comprises six (6) magnetic coils 360(1)-360(6) positioned around a surgical region 361. In the example of FIG. 3A, the coils 360(1)-360(6) are arranged as three pairs of mutually orthogonal Helmholtz coils. More specifically, coils 360(1) and 360(2) form a first pair 363(1) of co-axial Helmholtz coils that are arranged about an X axis 362, while coils 360(3) and 360(4) form a second pair 363(2) of co-axial Helmholtz coils that are arranged about a Y axis 364. Coils 360(5) and 360(6) form a third pair 363(3) of co-axial Helmholtz coils that are arranged about a Z axis 366. The intersecting X, Y, and Z axes form a Cartesian coordinate system having an origin at the center of the surgical region 361. As shown in FIG. 3A, the two coils of each pair 363(1), 363(2), and 363(3) are disposed on opposite sides of the surgical region 361. The coils 360(1)-360(6) are arranged to permit insertion of the head of the recipient 352 into the surgical region 361. The 360(1)-360(6) may be stand-alone coils or arranged on a structure.

The coils 360(1)-360(6) each comprise a plurality of turns of a conductor. The coils 360(1)-360(6) also each comprise equal numbers of turns and the two coils of each pair are wound co-directionally with one another. For example, both coils 360(1) and 360(2) arranged about the X axis 362 have windings that wrap around the X axis 362 in a counterclockwise direction (viewed with respect to the positive end of the X axis). The coils 360(3) and 360(4) arranged about Y axis 364, as well as the coils 360(5) and 360(6) arranged about Z axis 366 may have similar co-directional winding arrangements.

The external subsystem 354 of FIG. 3A also comprises a coil driving system 370 that is electrically connected to each of the coils 360(1)-360(6). Coil driving system 370 is configured to selectively pass alternating current through the coils (i.e., drive or excite the coils) to induce magnetic fields within the surgical region 361. Coil driving system 370 is connected to, and operates under the control of, a control device 376. The control device 376 may be a computing device such as a desktop computer, laptop computer, tablet computer, etc.

Internal subsystem 356 comprises one or more internal coils 372 that are configured to be implanted in the recipient 352. As described further below, embodiments of the present invention may include a plurality of coils configured to be implanted in a recipient. However, for ease of illustration, the example of FIG. 3A is described with reference to the use of a single coil 372 that is disposed in the stimulating assembly 118 of the internal component 142. Because the sensing coil 372 is disposed in the stimulating assembly 118, the sensing coil is sometimes referred to herein as an assembly coil. Assembly coil 372 comprises a plurality of turns of a conductor and is electrically connected to transceiver unit 132.

In operation, a surgeon or other user will operate the control device 370 to activate coil driving system 370 and energize coils 360(1)-360(6) to generate three separately distinguishable magnetic fields within the surgical region 361. In one embodiment of FIG. 3A, a frequency division scheme is used to generate the three separately distinguishable magnetic fields within the surgical region 361. That is, current signals of three different frequencies are used to excite a respective one of the pairs 363(1), 363(2), and 363(3) in order to generate the three separately distinguishable magnetic fields. In one specific such embodiment, coils 360(1) and 360(2) in pair 363(1) are energized with a current having a frequency of 35 Kilohertz (kHz), coils 360(3) and 360(4) in pair 363(2) are energized with a current having a frequency of 45 kHz, and coils 360(5) and 360(6) in pair 363(3) are energized with a current having a frequency of 55 kHz. It is to be appreciated that these specific frequencies are merely illustrative and that other combinations of frequencies may be used in different embodiments.

It is also to be appreciated that the use of current signals having different frequencies is merely one exemplary method that may be used in embodiments of the present invention to generate distinguishable magnetic fields within the surgical region 361. For example, alternative embodiments may use a time division scheme where only one pair of external coils is driven at a given time. In such embodiments, one pair of coils, such as pair 363(1) is driven while the other two pairs 363(2) and 363(3) remain off. Next, the current through pair 363(1) is stopped and the next pair of coils, such as pair 363(2), is excited while the other pairs 363(1) and 363(3) remain off. Subsequently, the current through pair 363(2) is stopped and the next pair of coils 363(3) is excited while the other pairs 363(1) and 363(2) remain off. This process continues in a serial fashion for a period of time.

It will also be appreciated that one of the many other methods of distinguishing potentially interfering magnetic field signals may be used in further embodiments of the present invention. Such methods include, but are not limited to, phase modulation, digital signature encoding and spread spectrum techniques.

In FIG. 3A, the magnetic field generated by pair 363(1) is represented by arrow 365(1) and has a direction of travel along the X axis 362 (i.e., the direction of the magnetic field is along the X axis). Similarly, the magnetic field generated by pair 363(2) is represented by arrow 365(2) and has a direction along the Y axis 364, while the magnetic field generated by pair 363(3) is represented by arrow 365(3) and has a direction along the Z axis 366.

FIG. 3A illustrates an example where a surgeon is attempting to implant stimulating assembly 118 into the cochlea 140 of recipient 352. As such, the stimulating assembly 118, having assembly coil 372 disposed therein, is positioned within surgical region 361. As a result, regardless of the method used to excite the external coils 360(1)-360(6) (e.g., frequency or time division), the three magnetic fields generated by the coil pairs 363(1), 363(2), and 363(3) will be sensed by the assembly coil 372.

Figure 3B:
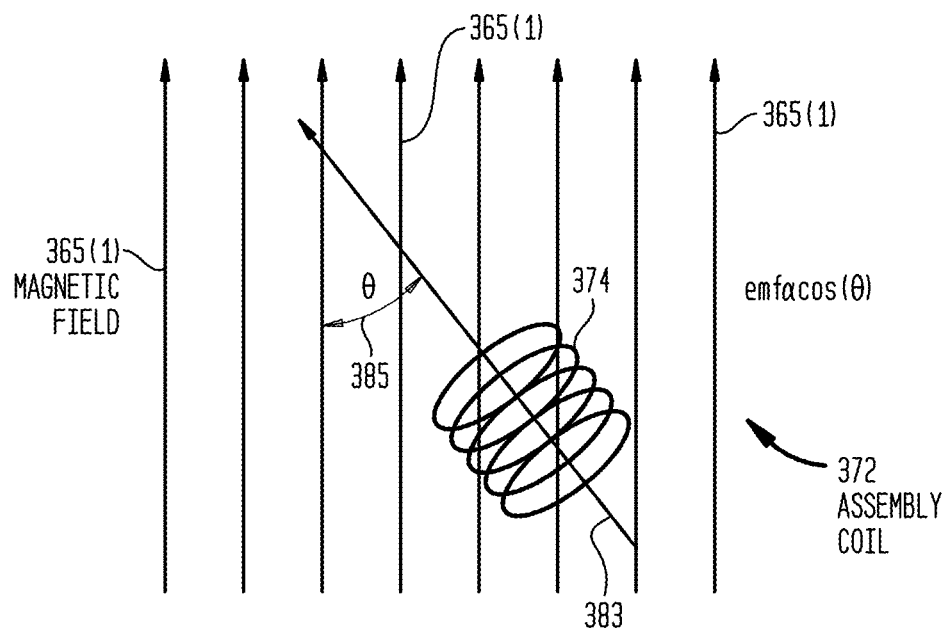
FIG. 3B is a schematic diagram illustrating the angular orientation of an assembly coil relative to a magnetic field in accordance with embodiments of the present invention.

FIG. 3B is a perspective view of assembly coil 372 of FIG. 3A relative to a sensed magnetic field 365(1). The assembly coil 372 comprises a plurality of substantially parallel turns of a conductor that are arranged about a central coil axis 383. Also shown in FIG. 3B is magnetic field 365(1) that has a direction that differs from the orientation of assembly coil 372 by an angle theta (θ). This angle represents the angular orientation of assembly coil 372 (i.e., the orientation of central coil axis 383) relative to the direction of magnetic field 365(1).

When a magnetic field, such as magnetic field 365(1), is sensed by the assembly coil 372, the magnetic field will cause current to flow within the assembly coil 372, thereby inducing a voltage (electromagnetic force (emf)) at the assembly coil. The induced voltage within the assembly coil 372 is proportional to the angular orientation of the assembly coil 372 to the direction of the sensed magnetic field 365(1). More specifically, the proportionality of the voltage to the magnetic filed is a cosine relationship as shown below in Equation 1.

$$\text{emf } \alpha \cos(\theta) \quad \text{Equation 1}$$

The voltages generated by the assembly coil 372 are detected by acquisition hardware 388 in the transceiver/stimulator unit and are transcutaneously transferred from internal coil 134 to external coil 130 for subsequent forwarding to visualization subsystem 359.

In the embodiments of FIG. 3A, visualization subsystem 358 is embodied in control device 376. Control device 376 is a computing device that comprises a plurality of interfaces/ports 378(1)-378(N), a memory 380, a display device (e.g., screen) 382, a processor 384, and a user interface 386.

The interfaces 378(1)-378(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 3A, interface 378(3) is connected to the coil driving system 370, while interface 378(1) is connected to external coil 130 and/or a external device in communication with the external coil. Interface 378(1) may be configured to receive the voltage signals via a wired or wireless connection (e.g., telemetry).

The voltages generated at the assembly coil 372 and forwarded to the control device 376 are filtered prior to, or following, receipt at the control device 376 with one or analog or digital filters. FIG. 3A illustrates an example where control device 376 includes filtering logic 390 to perform digital filtering operations.

As noted above, the voltages represent the angular orientation of assembly coil 372 (i.e., the orientation of the central axis 383 extending through the turns) relative to sensed magnetic fields. The filtering is configured to differentiate between the various sensed magnetic fields (e.g., differentiate the frequencies of the external coils) so that the voltage corresponding to each pair 363(1), 363(2), and 363(3) of external coils can be extracted independently. That is, once filters are applied to the sampled data, three separate signals are generated that provide the relative angular orientation of the assembly coil 372 to each of the X, Y, and Z axes corresponding to the directions of the magnetic fields 365(1), 365(2), and 365(3), respectively. In FIG. 3A, the external coil pairs 363(1), 363(2), and 363(3) are orthogonal to one another to ensure minimal interference while also allowing for direct extraction of the angle dependent properties.

As suggested by Equation 2, below, the outputs from the digital filtering take the form of three voltage magnitudes and phases corresponding to the three orthogonal axes (X, Y, and Z) of the external subsystem 354. This data may then be used by the imaging logic 392 to generate a reconstructed three dimensional virtual stimulating assembly for display at display device 382.

$$V_x(\theta) = V_{x(max)} \times \cos(\theta), \quad \text{Equation 2}$$

In one example, the imaging logic 392 includes a reconstruction algorithm that takes into account the helical nature of the anatomical cochlea by assuming a constant radius fit between assembly coil positions. The angle and phase data is only available at discrete points along the length of a stimulating assembly (i.e., at locations where assembly coils are present). As such, interpolation is used to extrapolate/estimate the position/shape of the portions of the stimulating assembly lying between the discrete and the information is presented to the surgeon in one or more different manners. In certain embodiments, the information regarding the orientation, position, and/or shape of the stimulating assembly may be visually presented to the surgeon. This visual presentation may comprise, for example, a three-dimensional or two-dimensional presentation on a display screen. In other embodiments, audible, haptic (tactile), or other types of feedback may be presented to the surgeon. For example, an audible warning may be generated if it is determined that an event has occurred or is about to occur (e.g., audible warning may be generated when the tip of the stimulating assembly becomes stuck or has begun to perforate the basilar membrane). Alternatively, vibrations or a buzzing may be generated if it is determined that an event has occurred or is about to occur. It is also to be appreciated that different types of feedback may be used in combination with one another (i.e., a visual presentation on a display screen along with an audible warning when an event has occurred or is about to occur).

In the embodiments of FIG. 3A, it is the orientation of the assembly coil 372 within surgical region 361 (and not the position of the assembly coil 372) that is directly determined based on sensed magnetic fields. However, embodiments of the present invention include techniques to indirectly determine the position of the stimulating assembly within the cochlea 140.

In one such embodiment, a pre-selected location within the surgical region 361 is used as a base point, and the position of the assembly coil 372 within the surgical region may be determined relative to this pre-selected location. More particularly, the implantation imaging system 350 first captures the magnetic field information (i.e., stimulate, sense, filter, and store outputs) when, for example, the assembly coil 372 or the distal end of the stimulating assembly is at the pre-selected location.

When the assembly coil 372 is inserted and magnetic field information is captured, the imaging logic 392 is configured to use the stored magnetic field information to determine the trajectory of the stimulating assembly 118 and therefore plot the position relative to the pre-selected location.

The pre-selected location may be a location within the surgical region 361. In one example, the pre-selected location corresponds to a point of an organ of the recipient 352, such as the cochleostomy 122 in cochlea 140.

In certain embodiments, the imaging logic 392 is configured to add a representation of the cochlea 140 to the display device 382 to allow the surgeon to visualize where the stimulating assembly 118 is in relation to the structures of the cochlea 140. That is, similar to the examples of FIGS. 11 and 12 described below, the representation of the stimulating assembly is shown within (inside) the representation of the cochlea to mimic what is occurring within the recipient during the implantation procedure. Additionally, the representation of the cochlea 140 may be aligned with the pre-selected location so that the display accurately reflects the initial known position of the stimulating assembly 118 relative to the cochlea 140. For example, the representation of the cochlea may have a cochleostomy that is aligned with the previously determined position of the cochleostomy 122 in cochlea 140. The representation of the cochlea may be generated based on the dimensions of a typical cochlea or generated based on previously determined dimensions of the recipient's actual cochlea (e.g., through preoperative imaging such as MRI, X-ray, etc.).

In the embodiments of FIG. 3A, user interface 386 may comprise any combination of user input controls, such as a keyboard, a mouse, etc. In certain embodiments, user interface 386 and display device 382 may be a unitary element (i.e., a touchscreen).

Memory 380 may comprise read only memory (ROM), random access memory (RAM), magnetic disk storage media devices, optical storage media devices, flash memory devices, electrical, optical, or other physical/tangible memory storage devices. The processor 384 is, for example, a microprocessor or microcontroller that executes instructions for the filtering logic 390 and imaging logic 392. Thus, in general, the memory 380 may comprise one or more tangible (non-transitory) computer readable storage media (e.g., a memory device) encoded with software comprising computer executable instructions and when the software is executed (by the processor 384) it is operable to perform the operations described herein in connection with filtering logic 390 and imaging logic 392.

FIG. 3A illustrates an embodiment in which external subsystem 354 comprises three pairs 363(1), 363(2), and 363(3) of Helmholtz coils. It is to be appreciated that external subsystem 354 may have different arrangements in alternative embodiments of the present invention. For example, embodiments of the present invention may use Maxwell coils in addition to, or in place of, the Helmholtz coils. In a Maxwell coil arrangement, a third larger-diameter coil may be added between two Helmholtz coils to reduce the variance of the field on the axis of the coils.

Figure 4:
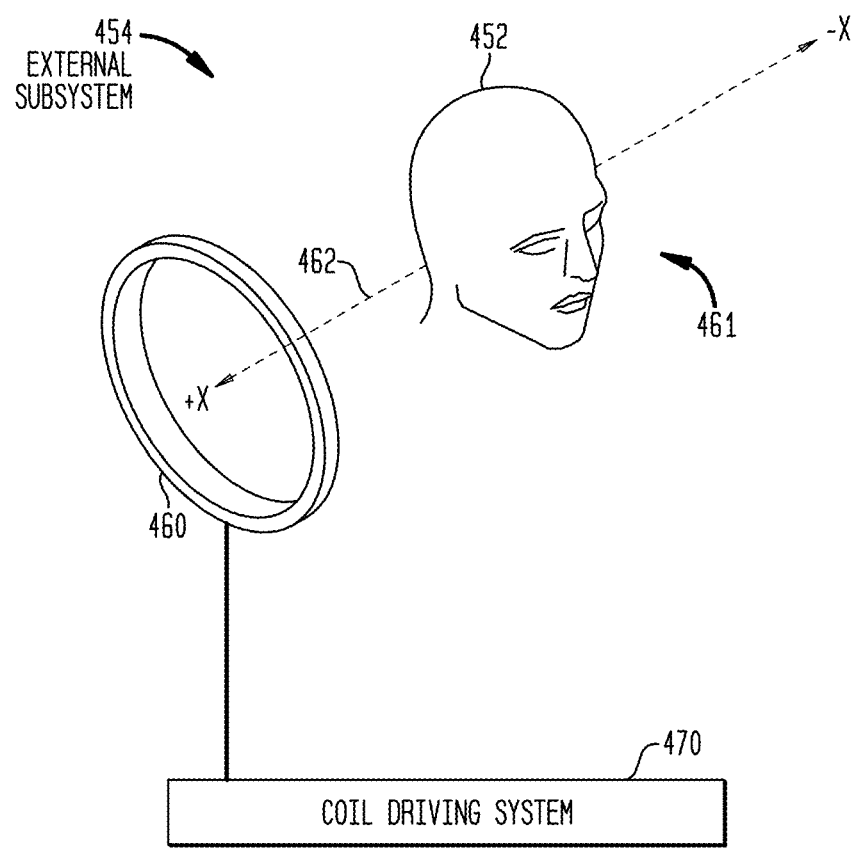
FIG. 4 is schematic diagram of an external subsystem of an implantation imaging system in accordance with embodiments of the present invention.

FIG. 4 illustrates an embodiment of the present invention where an external subsystem 454 includes a single external coil 460 and a coil driving system 470. For ease of illustration, the internal subsystem and the visualization subsystem that may be used in conjunction with the external subsystem 454 have been omitted from FIG. 4. It is to be appreciated that the internal subsystem and the visualization subsystem may be implemented as described above with reference to FIG. 3A.

The coil 460 comprises one or more turns of wire that are arranged around an axis 462. In this example, axis 462 is an X axis relative to the orientation of a recipient's head 452 within the surgical region 461. In this embodiment, the single external coil 460 is used to generate a time varying magnetic field within surgical region 461 which is sensed by one or more assembly coils (not shown) disposed within the recipient's head 452. More specifically, similar to the embodiments of FIG. 3A, the magnetic field generated by coil 460 induces a voltage at each of the one or more assembly coils which is relative to the angular orientation of the assembly coils to the magnetic field. As such, this voltage generated at each of the assembly coils may be used to determine the orientation of the assembly coils to the magnetic field.

Figure 5:
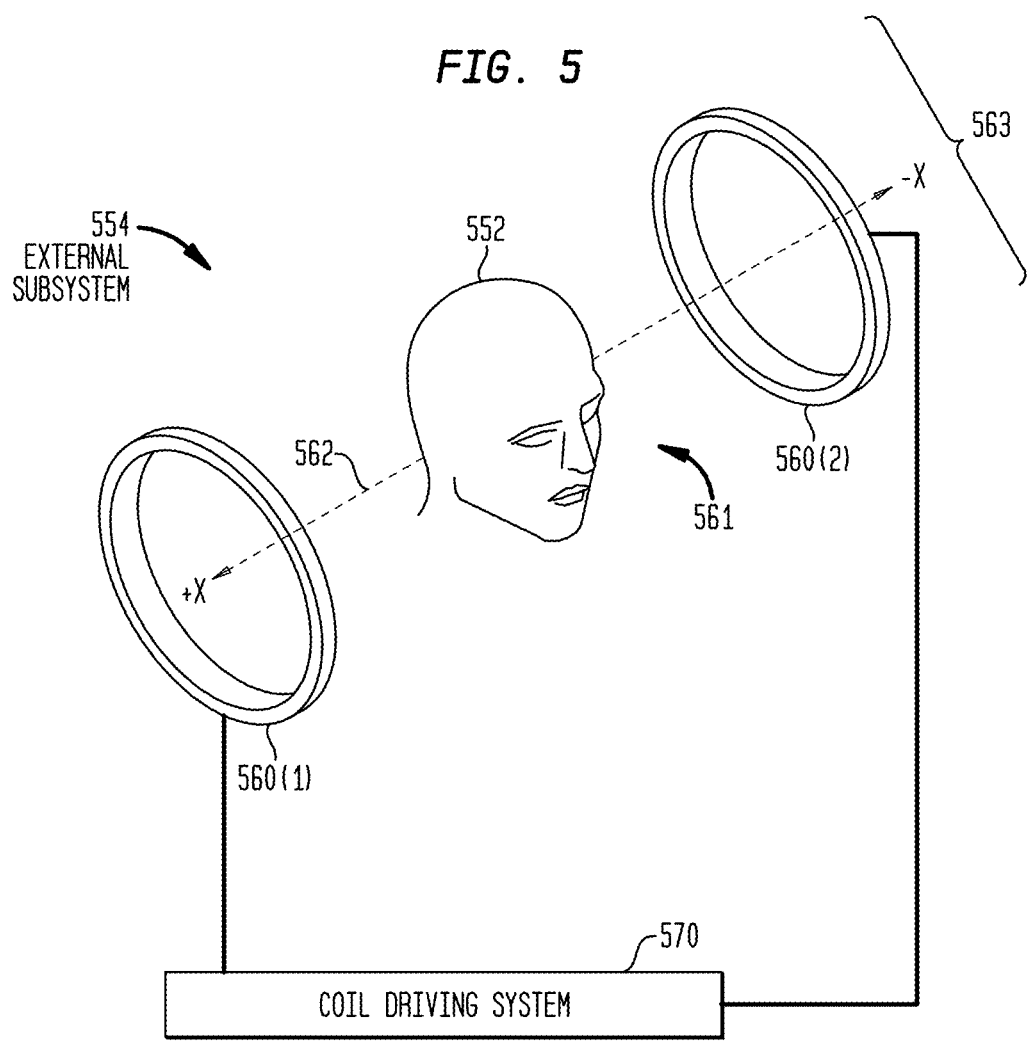
FIG. 5 is schematic diagram of an external subsystem of an implantation imaging system in accordance with embodiments of the present invention.

FIG. 5 illustrates another embodiment where an external subsystem 554 of an implantation imaging system includes a single pair 563 of external coils 560(1) and 560(2) and a coil driving system 570. For ease of illustration, the internal subsystem and the visualization subsystem that may be used in conjunction with the external subsystem 554 have been omitted from FIG. 5. It is to be appreciated that the internal subsystem and the visualization subsystem may be implemented as described above with reference to FIG. 3A.

The coils 560(1) and 560(2) each comprise one or more turns of wire that are arranged around an axis 562. In this example, axis 562 is an X axis relative to the orientation of a recipient's head 552 within the surgical region 561. In this embodiment, the pair 563 of external coils 560(1) and 560(2) is used to generate a time varying magnetic field within surgical region 561 which is detected by one or more assembly coils (not shown) disposed within the recipient's head 552. More specifically, similar to the embodiments of FIG. 3A, the magnetic field generated by coils 560(1) and 560(2) induces a voltage at the one or more assembly coils which is relative to the angular orientation of the assembly coils to the magnetic field. As such, the voltages generated by each of the assembly coils may be used to determine the orientation of the assembly coils to the magnetic field. In this embodiment less information about the three dimensional orientation of the coil is available. However, it may still be possible to deduce the coil orientation in one or more axes by using additional information such as the orientation of adjacent coils and the expected anatomy of the electrode assembly location.

Figure 6:
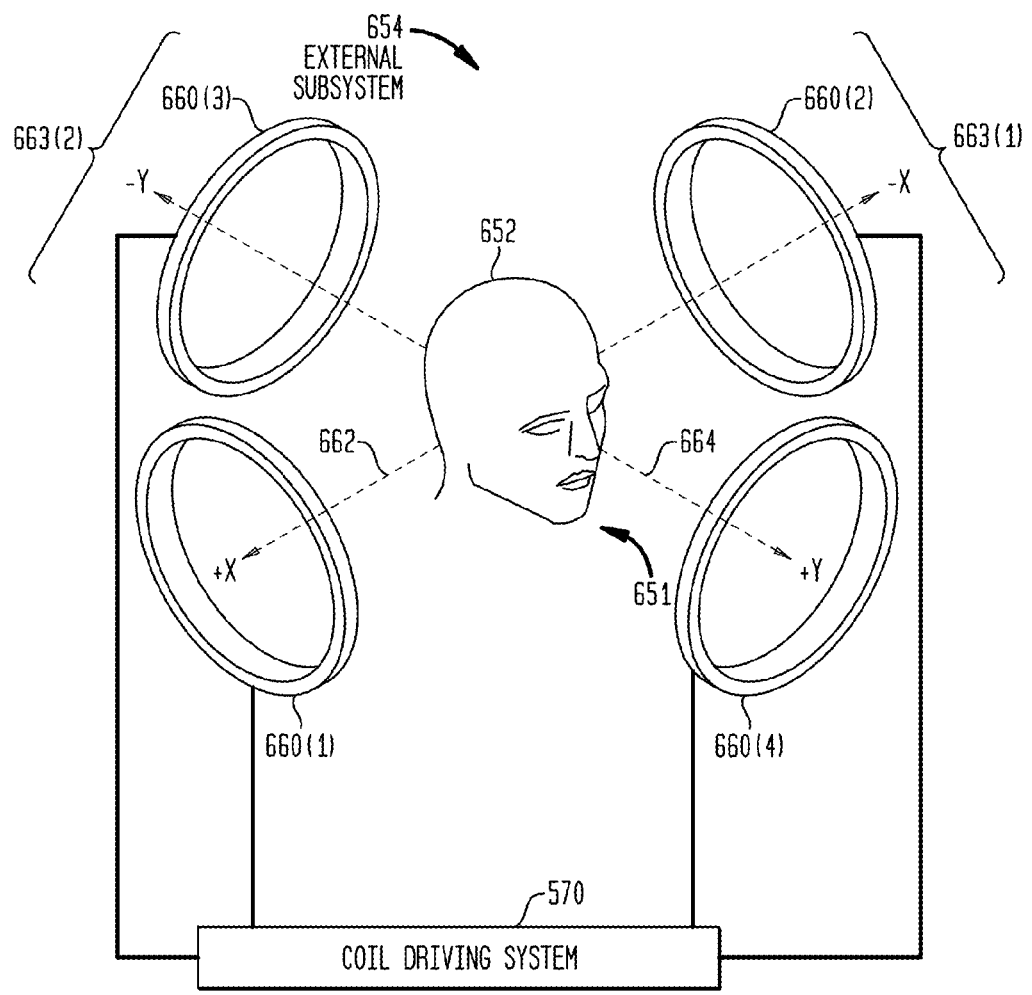
FIG. 6 is schematic diagram of an external subsystem of an implantation imaging system in accordance with embodiments of the present invention.

FIG. 6 illustrates another embodiment where an external subsystem 654 of an implantation imaging system includes four external coils 660(1)-660(4) as well as a coil driving system 670. The external coils 660(1) and 660(2) form a first pair 663(1) of coils, while coils 660(3) and 660(4) form a second pair 663(2) of coils. For ease of illustration, the internal subsystem and the visualization subsystem that may be used in conjunction with the external subsystem 654 have been omitted from FIG. 6. It is to be appreciated that the internal subsystem and the visualization subsystem may be implemented as described above with reference to FIG. 3A.

The coils 660(1) and 660(2) each comprise one or more turns of wire that are arranged around a first axis 662. Similarly, the coils 660(3) and 660(4) also each comprise one or more turns of wire that are arranged around a second axis 664. In this example, axis 662 is an X axis relative to the orientation of a recipient's head 652 within the surgical region 661, while axis 664 is a Y axis relative to the orientation of a recipient's head 652 within the surgical region 661.

In this embodiment, the coil pairs 663(1) and 663(2) of external coils are used to generate two distinguishable time varying magnetic fields within surgical region 661. These magnetic fields are detected by one or more assembly coils (not shown) disposed within the recipient's head 652. More specifically, similar to the embodiments of FIG. 3A, the magnetic fields generated by coil pairs 663(1) and 663(2) induce voltages at the one or more assembly coils that are relative to the angular orientation of the assembly coils to the magnetic fields. As such, the voltages generated by each of the assembly coils may be used to determine the orientation of the assembly coils to the magnetic field.

FIGS. 4, 5, and 6 illustrate several exemplary external subsystems that may be used in an implantation imaging system of embodiments of the present invention. It is to be appreciated that external subsystems having different arrangements to generate magnetic fields may also be used in further embodiments of the present invention.

The above embodiments of FIGS. 3A, 3B, 4, 5, and 6 have been primarily described with reference to the use of external coils to generate magnetic fields that are sensed by coils disposed within a recipient. It is to be appreciated that, in alternative embodiments, the coils disposed within the recipient may be energized to generate magnetic fields that are detected by external coils (i.e., the internal coils operate as transmitting coils, while the external coils operate as sensing coils). In one specific such example, the external coils can be arranged in three orthogonal axes (x, y and z) so that by measuring the relative magnitude of the signals in each coil the direction of a magnetic field generated by an internal coil can be determined. The determined direction of the magnetic field, in combination with the known orientation of the external coils, can be used to determine the orientation of the transmitting coil within the recipient.

FIG. 3A illustrates an embodiment of the present invention in which the internal subsystem includes one assembly coil for detection of external magnetic fields. It is to be appreciated that internal subsystems in accordance with embodiments of the present invention may use different numbers of assembly coils in a number of different arrangements.

Figure 7:
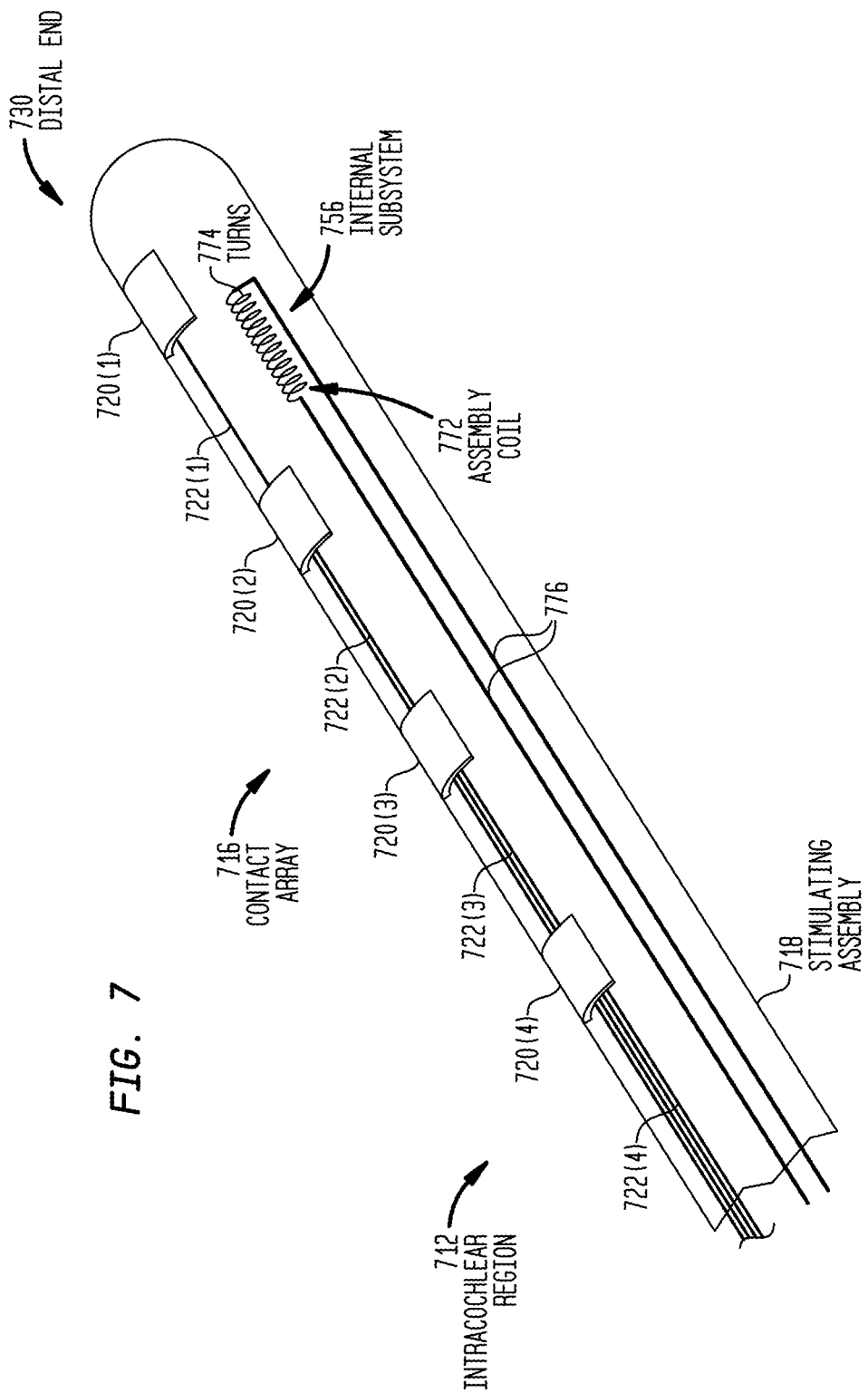
FIG. 7 is a perspective view of an internal subsystem of an implantation imaging system in accordance with embodiments of the present invention.

FIG. 7 illustrates one embodiment of an internal subsystem 756 for use in implantation of a stimulating assembly 718. Stimulating assembly 718 comprises an extra-cochlear region (not shown) and an intracochlear region 712 configured to be implanted in recipient's cochlea. For ease of illustration, only a portion of intracochlear region 712 is shown in FIG. 7.

Stimulating assembly 718 comprises a contact array 716 that includes a plurality of stimulating contacts 720(1)-720(4). Present commercial devices offered by the industry use electrical contacts, but Cochlear™ and others are engaged in research on the potential uses of optical stimulation alone or in conjunction with electrical or other stimulation mechanisms. As such, the stimulating contacts 720(1)-720(4) may be optical or electrical contacts. For ease of illustration, only electrical contacts are shown in FIG. 7. The electrical contacts 720(1)-720(4) are each separately connected to a stimulator/transceiver unit (not shown) via wires 722(1)-722(4), respectively.

In the embodiment of FIG. 7, internal subsystem 756 comprises a single assembly coil 772 disposed in the distal end/region (tip) 730 of stimulating assembly 718. The assembly coil 772 comprises a plurality of turns 774 of a wire 776 that extends from the stimulator/transceiver unit. At the distal end of the assembly coil 772, the wire 776 returns to the stimulator/transceiver unit.

As noted, FIG. 7 illustrates an embodiment where the distal end of the assembly coil 772 is connected to the stimulator/transceiver unit. In an alternative embodiment, the distal end of the assembly coil 772 may be connected to one of the electrical contacts, such as electrical contact 720(1). In such embodiments, that electrical contact 720(1) is also still connected to wire 722(1) (i.e., the electrical contact 720(1) has two wires leading to it, one to each end).

In one embodiment, during implantation of stimulating assembly 718 into a recipient's cochlea, one or more coils disposed adjacent to the recipient's head will generate magnetic fields that induce voltages at assembly coil 772. As noted above, the induced voltages are directly proportional to the orientation of the assembly coil 772 to the direction of the stimulating magnetic fields. The induced voltages are provided to the stimulator/transceiver unit via wire 776 for subsequent processing by a visualization subsystem (not shown) as described above.

In another embodiment, during implantation of stimulating assembly 718 into a recipient's cochlea, the assembly coil 772 is energized so as to generate a magnetic field. This magnetic field is configured to induce current to flow in one or more external coils (not shown) disposed adjacent to the recipient's head. The flow of current in each of the one or more external coils is directly proportional to the orientation of the respective external coil to the direction of the magnetic field, thereby resulting in the generation of a voltage that represents the orientation of the respective external coil to the direction of the magnetic field. The voltage is provided to visualization subsystem (not shown) for subsequent processing as described above.

Figure 8:
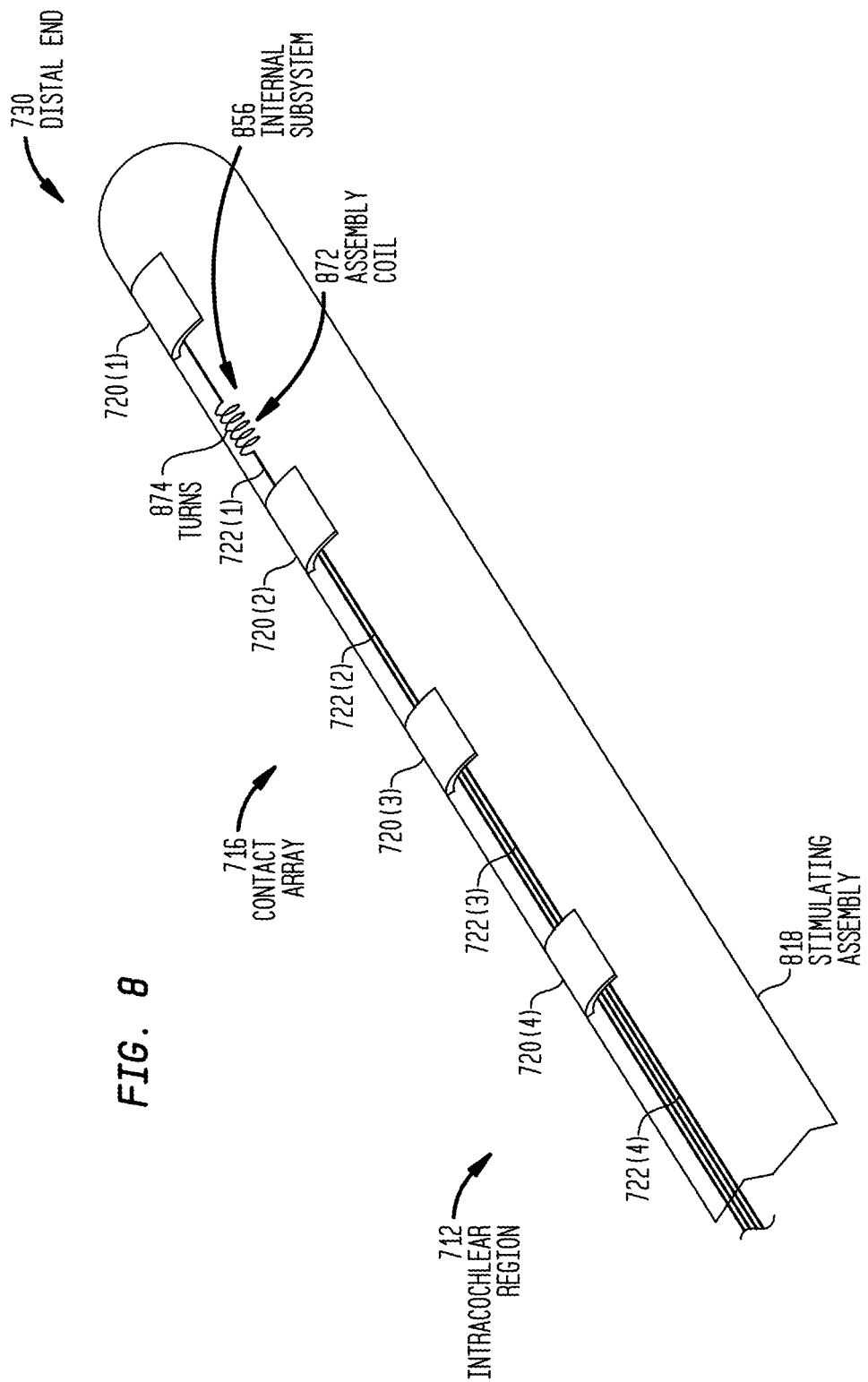
FIG. 8 is a perspective view of an internal subsystem of an implantation imaging system in accordance with embodiments of the present invention.

FIG. 8 illustrates another embodiment of an internal subsystem 856 for use in implantation of a stimulating assembly 818. Similar to the embodiments of FIG. 7, stimulating assembly 818 comprises an extra-cochlear region (not shown) and an intracochlear region 712 configured to be implanted in recipient's cochlea. For ease of illustration, only a portion of intracochlear region 712 is shown in FIG. 8.

Stimulating assembly 818 comprises a contact array 716 that includes a plurality of electrical contacts 720(1)-720(4) that are each separately connected to a stimulator/transceiver unit (not shown) via wires 722(1)-722(4), respectively.

In the embodiment of FIG. 8, internal subsystem 856 comprises a single assembly coil 872 disposed in the distal end/region 730 of stimulating assembly 818. The assembly coil 872 comprises a plurality of turns 774 of wire 722(1) that extends from the electrical contact 720(1) to the stimulator/transceiver unit. That is, in contrast to the embodiments of FIG. 7 where the assembly coil 772 and its associated wire 776 are both separate from the contact wires, in the embodiments of FIG. 8 the assembly coil 872 is integrated with the contact wire 722(1). As such, in the embodiments of FIG. 8, no additional wires are required to be fed into the stimulating assembly for use as an internal subsystem.

In one embodiment, during implantation of stimulating assembly 718 into a recipient's cochlea, one or more coils disposed adjacent to the recipient's head will generate magnetic fields that induce voltages at assembly coil 772. The induced voltages are directly proportional to the orientation of the assembly coil 772 to the direction of the stimulating magnetic fields. The voltages are sensed on the wire 722(2) using sensing electronics provided in the stimulator/transceiver unit. The ground (reference) input for the sensed signal is the electrical contacts 720(1)-720(4) with no inbuilt coils shorted together to produce a single common ground electrode. The voltages are provided to a visualization subsystem (not shown) for subsequent processing as described above.

In another embodiment, during implantation of stimulating assembly 818 into a recipient's cochlea, the assembly coil 872 is energized so as to generate a magnetic field. This magnetic field is configured to induce current to flow in one or more external coils (not shown) disposed adjacent to the recipient's head. The flow of current in each of the one or more external coils is directly proportional to the orientation of the respective external coil to the direction of the magnetic field, thereby resulting in the generation of a voltage that represents the orientation of the respective external coil to the direction of the magnetic field. The voltage signal is provided to visualization subsystem (not shown) for subsequent processing as described above.

Figure 9:
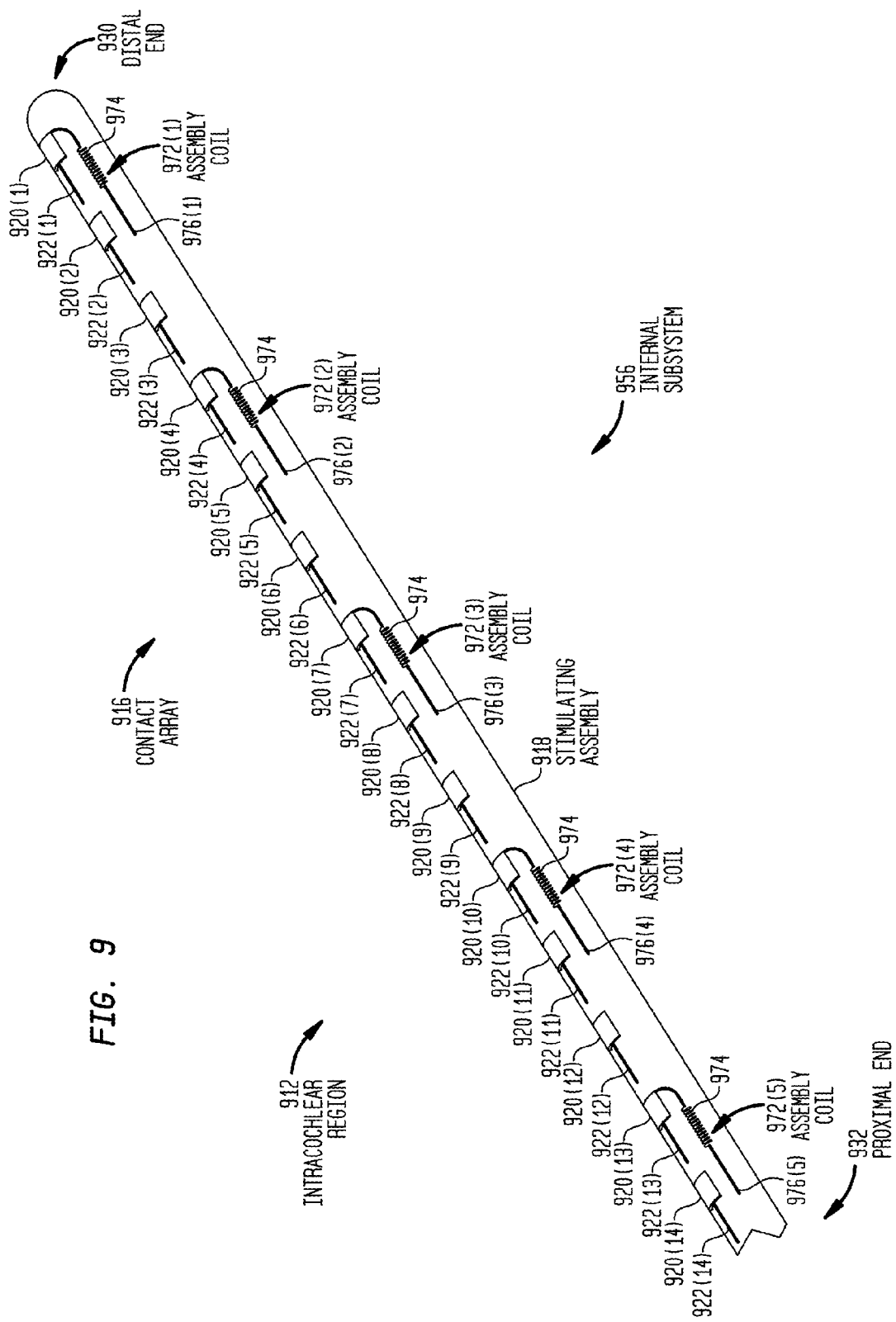
FIG. 9 is a perspective view of an internal subsystem of an implantation imaging system in accordance with embodiments of the present invention.

FIG. 9 illustrates another embodiment of an internal subsystem 956 for use in implantation of a stimulating assembly 918. Stimulating assembly 918 comprises an extra-cochlear region (not shown) and an intracochlear region 912 configured to be implanted in recipient's cochlea. Intracochlear region 912 comprises a distal end 930 and a proximal end 932.

Stimulating assembly 918 comprises a contact array 916 that includes a plurality of stimulating contacts 920(1)-920(14). The stimulating contacts 920(1)-920(14) may be optical or electrical contacts. For ease of illustration, only electrical contacts are shown in FIG. 9. The electrical contacts 920(1)-920(14) are each separately connected to a stimulator/transceiver unit (not shown) via wires 922(1)-922(14), respectively.

In the embodiment of FIG. 9, internal subsystem 956 comprises a plurality of assembly coils 972(1)-972(5) disposed in the stimulating assembly 918. The assembly coils 972(1)-972(5) are longitudinally spaced along the elongate length of the stimulating assembly 918 such that a first assembly coil 972(1) is disposed in the distal end 930 and a fifth assembly 972(5) is disposed in the proximal end 932. The second, third, and fourth assembly coils 972(2), 972(3), and 972(4) are spaced between the distal end 930 and the proximal end 932. Each assembly coil 972(1)-972(5) comprises a plurality of turns 974 of a wire 976(1)-976(5), respectively, that extends from the stimulator/transceiver unit. The distal ends of the coils 972(1), 972(2), 972(3), 972(4), and 972(5) are connected to electrical contacts 920(1), 920(4), 920(7), 920(10), and 920(14), respectively. In alternative embodiments, the distal ends of the coils 972(1)-972(5) may be connected to the stimulator/transceiver unit.

In one embodiment, during implantation of stimulating assembly 918 into a recipient's cochlea, one or more coils disposed adjacent to the recipient's head generate magnetic fields that induce voltages at each of the assembly coils 972(1)-972(5). The voltages at each assembly coil 972(1)-972(5) are directly proportional to the orientation of the respective coil to the direction of the magnetic fields. The voltages are provided to the stimulator/transceiver unit for subsequent processing, as described above, by a visualization subsystem (not shown).

In another embodiment, during implantation of stimulating assembly 918 into a recipient's cochlea, the assembly coils 972(1)-972(5) are energized so as to generate separately distinguishable magnetic fields (e.g., through a frequency division scheme or a time division scheme as described above). The magnetic fields are configured to induce current to flow in one or more external coils (not shown) disposed adjacent to the recipient's head. The flow of current in each of the one or more external coils is directly proportional to the orientation of the respective external coil to the direction of the detected magnetic field, thereby resulting in the generation of a voltage that represents the orientation of the respective external coil to the direction of the detected magnetic field. The voltage signal is provided to visualization subsystem for subsequent processing as described above.

Figure 10:
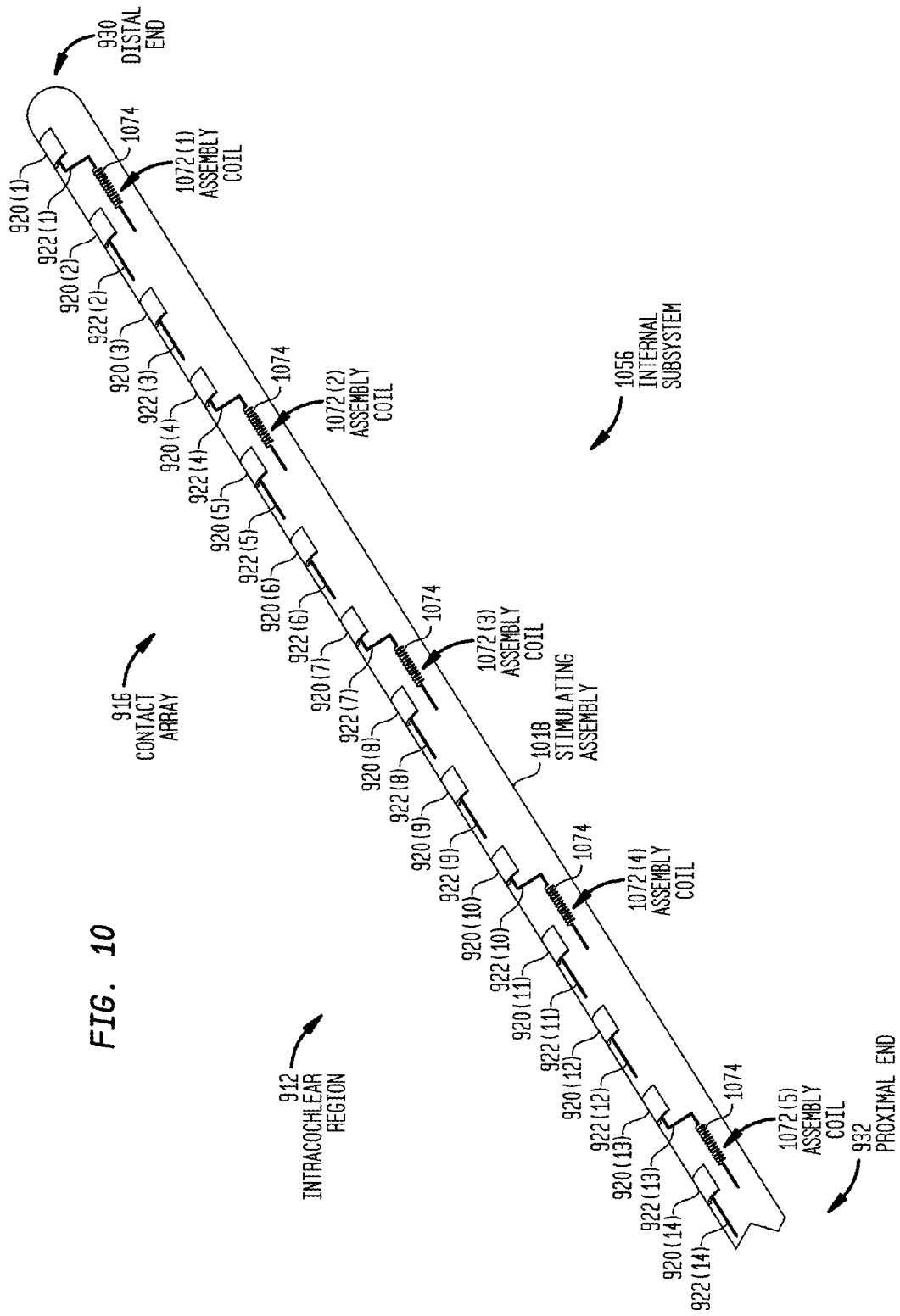
FIG. 10 is a perspective view of an internal subsystem of an implantation imaging system in accordance with embodiments of the present invention.

FIG. 10 illustrates another embodiment of an internal subsystem 1056 for use in implantation of a stimulating assembly 1018. Similar to the embodiments of FIG. 9, stimulating assembly 1018 comprises an extra-cochlear region (not shown) and an intracochlear region 912 configured to be implanted in recipient's cochlea. Intracochlear region 912 comprises a distal end 930 and a proximal end 932.

Stimulating assembly 1018 comprises a contact array 916 that includes a plurality of electrical contacts 920(1)-920(14) that are each separately connected to a stimulator/transceiver unit (not shown) via wires 922(1)-922(14), respectively.

In the embodiment of FIG. 10, internal subsystem 1056 comprises a plurality of assembly coils 1072(1)-1072(5) disposed in the stimulating assembly 1018. The assembly coils 1072(1)-1072(5) are longitudinally spaced along the elongate length of the stimulating assembly 1018 such that a first assembly coil 1072(1) is disposed in the distal end 930 and a fifth assembly 1072(5) is disposed in the proximal end 932. The second, third, and fourth assembly coils 1072(2), 1072(3), and 1072(4) are spaced between the distal end 930 and the proximal end 932.

Each assembly coil 1072(1)-1072(5) comprises a plurality of turns 1074 of a wire that extends from the stimulator/transceiver unit. More specifically, assembly coil 1072(1) comprises a plurality of turns 1074 formed in wire 922(1) that extends from the stimulator/receiver unit to electrical contact 920(1). Assembly coil 1072(2) comprises a plurality of turns 1074 formed in wire 922(4) that extends from the stimulator/receiver unit to electrical contact 920(4), while assembly coil 1072(3) comprises a plurality of turns 1074 formed in wire 922(7) that extends from the stimulator/receiver unit to electrical contact 920(7). Assembly coil 1072(4) comprises a plurality of turns 1074 formed in wire 922(10) that extends from the stimulator/receiver unit to electrical contact 920(10), while assembly coil 1072(5) comprises a plurality of turns 1074 formed in wire 922(13) that extends from the stimulator/receiver unit to electrical contact 920(13). That is, in contrast to the embodiments of FIG. 9 where the assembly coils 972(1)-972(5) are separate from the contact wires, in the embodiments of FIG. 10 the assembly coils 1072(1)-1072(5) are integrated with the contact wires. As such, in the embodiments of FIG. 10, no additional wires are required to be fed into the stimulating assembly for use as an internal subsystem.

In one embodiment, during implantation of stimulating assembly 1018 into a recipient's cochlea, one or more coils disposed adjacent to the recipient's head will generate magnetic fields that induce voltages at the assembly coils 1072(1)-1072(5). The voltages at the assembly coils 1072(1)-1072(5) are directly proportional to the orientation of the assembly coils 1072(1)-1072(5) to the direction of the detected magnetic fields. The voltages at assembly coils 1072(1), 1072(2), 1072(3), 1072(4), and 1072(5) are sensed on the wires 922(1), 922(4), 922(7), 922(10), and 922(13), respectively, using sensing electronics provided in the stimulator/transceiver unit. The ground (reference) input for each sensed signal is one or more of the electrical contacts 920(1)-920(14) with no inbuilt coils shorted together to produce a single common ground electrode. Electrical contacts that are connected to wires that include assembly coils are not used as part of the ground electrode. The sensed voltage signal is provided to a visualization subsystem (not shown) for subsequent processing as described above.

In another embodiment, during implantation of stimulating assembly 1018 into a recipient's cochlea, the assembly coils 1072(1)-1072(5) are energized so as to generate separately distinguishable magnetic fields (e.g., through a frequency division scheme or a time division scheme as described above). The magnetic fields are configured to induce current to flow in one or more external coils (not shown) disposed adjacent to the recipient's head. The flow of current in each of the one or more external coils is directly proportional to the orientation of the respective external coil to the direction of the detected magnetic field, thereby resulting in the generation of a voltage that represents the orientation of the respective external coil to the direction of the detected magnetic field. The voltage signal is provided to visualization subsystem for subsequent processing as described above.

As noted above, FIGS. 7 and 8 illustrate internal subsystems that include one assembly coil, while FIGS. 9 and 10 illustrate internal subsystems that include five assembly coils. It is to be appreciated that internal subsystems in accordance with embodiments of the present invention may include any number of assembly coils. It is also to be appreciated that the assembly coils may be evenly or unevenly spaced within a stimulating assembly. For example, a plurality of assembly coils may be positioned at the distal end of the stimulating assembly to enable precise visualization of the distal region.

As noted, embodiments of the present invention provide a surgeon with information regarding the orientation, position, and/or shape of the stimulating assembly. This information may be presented, for example, through visual, audible, or tactile feedback. In certain embodiments, an implantation imaging may include a visualization system configured to use voltages sensed at the implanted assembly coils (or external coils) to display a visual representation of a stimulating assembly. Depending on the orientation and/or number of stimulus magnetic fields used and sensed, the visualization system may be configured to generate a two-dimensional or a three-dimensional image of a stimulating assembly. As noted above, in certain embodiments, the visualization subsystem may also be configured to display an image of a cochlea with the image of the stimulating assembly. In this manner, the surgeon can see an estimated orientation and location of the stimulating assembly within the cochlea.

Figure 11:
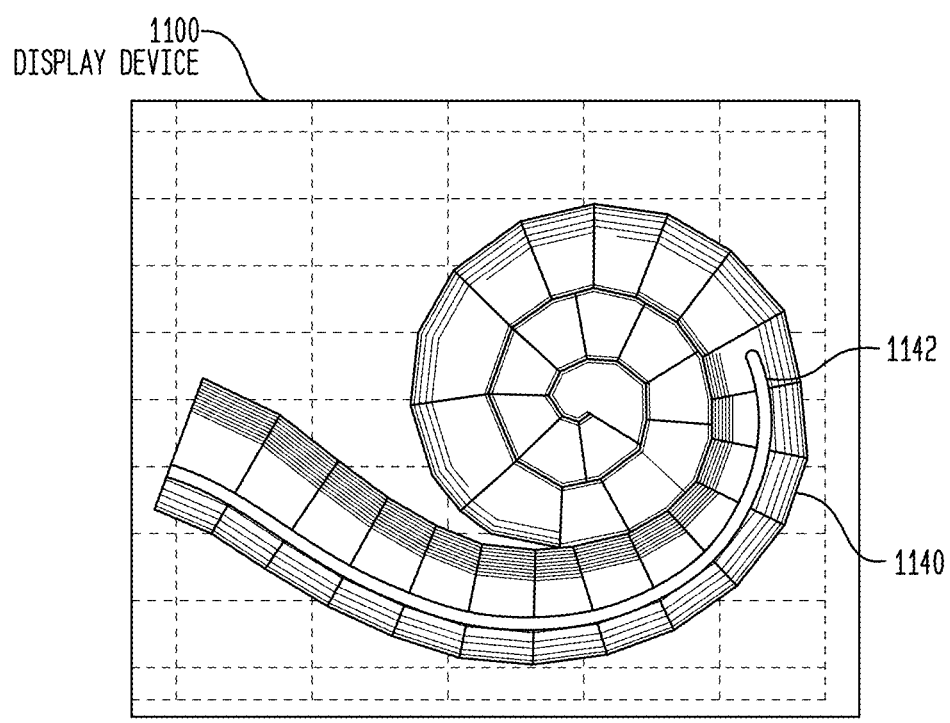
FIG. 11 is front view of a display screen configured to display a two-dimensional (2D) representation of a stimulating assembly and a cochlea in accordance with embodiments of the present invention.
Figure 12:
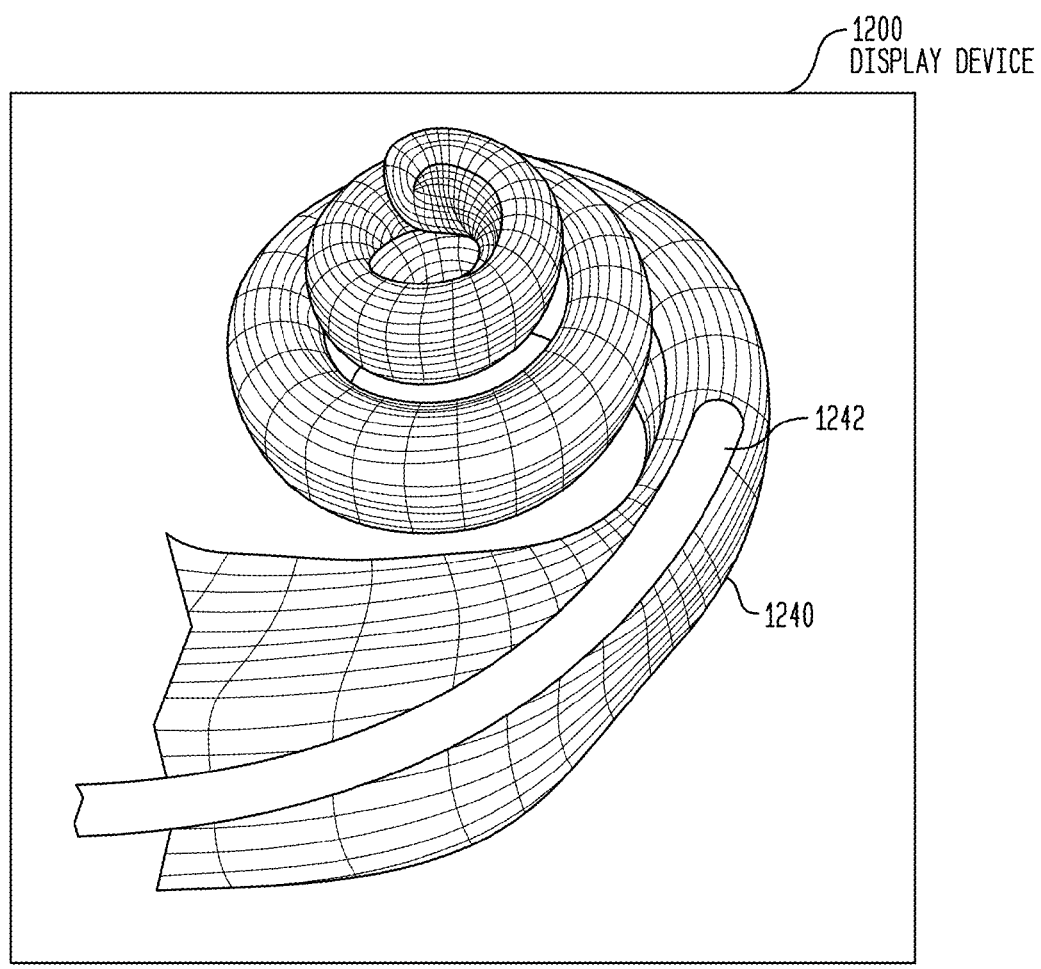
FIG. 12 is front view of a display screen configured to display a three-dimensional (3D) representation of a stimulating assembly and a cochlea in accordance with embodiments of the present invention.

For example, FIG. 11 is a schematic diagram of a display device 1100 that displays a two-dimensional representation 1102 of a cochlea and a two-dimensional representation 1104 of a stimulating assembly. Similarly, FIG. 12 is a schematic diagram of a display device 1200 that displays a three-dimensional representation 1202 of a cochlea and a three-dimensional representation 1204 of a stimulating assembly.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A system comprising:
    a first external coil arranged about a first axis and configured to generate a magnetic field within a surgical region;
    an intra-cochlear stimulating assembly configured to be inserted into a cochlea of recipient located in the surgical region, wherein the stimulating assembly comprises a plurality of assembly coils spaced along the length of the stimulating assembly, and wherein the plurality of assembly coils are each configured to detect the magnetic field generated by the first external coil and to generate a voltage based on the detected magnetic field; and
    a hardware processor configured to determine, based on the voltages detected at the plurality of assembly coils, an angular orientation of each of the plurality of assembly coils with respect to the first axis and, based on the determined angular orientations, extrapolate a shape of the stimulating assembly within the cochlea.

2. The system of claim 1, wherein the first external coil is configured to generate a magnetic field having a uniform strength across the surgical region to induce a voltage at the assembly coil.

3. The system of claim 1, wherein the plurality of assembly coils have a non-uniform spacing within the stimulating assembly.

4. The system of claim 1, further comprising:
    first, second, and third pairs of external coils each arranged about first, second, and third axes, respectively,
    wherein the plurality of assembly coils are each configured to detect the magnetic fields generated by the first, second, and third pairs of external coils and are each configured to generate three voltages based on the detected magnetic fields, and wherein the hardware processor is configured to use the three generated voltages from each of the plurality of assembly coils to determine an angular orientation of the corresponding assembly coil with respect to each of the first, second, and third axes and, based on the determined angular orientations, extrapolate the shape of the stimulating assembly within the cochlea.

5. The system of claim 1, further comprising:
    a second external coil arranged about a second axis and configured to generate a second magnetic field within the surgical region.

6. The system of claim 5, further comprising:
    a third external coil arranged about a third axis and configured to generate a third magnetic field within the surgical region.

7. The system of claim 1, further wherein the elongate assembly comprises a first assembly coil located at a distal end of the stimulating assembly, and wherein the hardware processor is configured to capture information about the magnetic field when the first assembly coil is positioned at a pre-selected location of the cochlea.

8. The system of claim 7, wherein the pre-selected location is an opening in the cochlea.

9. The system of claim 7, wherein the hardware processor is further configured to determine a location of each of the plurality of assembly coils with respect to the pre-selected location of the cochlea to determine a trajectory of the stimulating assembly and extrapolate the relative position of the stimulating assembly with respect to the pre-selected location.

10. The system of claim 9, wherein the hardware processor is further configured to display, on a display screen, the shape of the stimulating assembly and the relative position of the stimulating assembly with respect to the pre-selected location.

11. The system of claim 10, wherein the hardware processor is configured to display, on the display screen, a representation the cochlea and the shape of the stimulating assembly and the relative position of the stimulating assembly within the cochlea.

12. The system of claim 1, wherein the stimulating assembly a plurality of electrical stimulating contacts.

13. The system of claim 12, wherein the stimulating contacts are each electrically connected to a stimulator unit via separate wires and wherein one or more of the plurality of assembly coils are formed into one of the wires connecting the stimulating contacts to the stimulator unit.

14. The system of claim 12, wherein the stimulating contacts are each electrically connected to a stimulator unit via separate wires and wherein one or more of the plurality of assembly coils are formed separate from the stimulating contacts and the separate wires connecting the contacts to the stimulator unit.

15. A method comprising:
inserting, into the cochlea of a recipient located in a surgical region, an intra-cochlear stimulating assembly comprising a plurality of assembly coils spaced along the length of the stimulating assembly;
generating a magnetic field within the surgical region with a first external coil that is arranged about a first axis and positioned in proximity to the surgical region;
detecting the magnetic field at each of plurality of assembly coils such that a voltage is induced at each of the plurality of assembly coils; and
determining, based on the induced voltages, an angular orientation of each of the plurality of assembly coils with respect to the first axis and, based on the determined angular orientations, extrapolate a shape of the stimulating assembly within the cochlea.

16. The method of claim 15, wherein the stimulating assembly comprises a first assembly coil located at a distal end of the elongate assembly, and wherein the method further comprises:
capturing information about the magnetic field when the first assembly coil is positioned at a pre-selected location of the cochlea.

17. The method of claim 16, further comprising:
determining a location of each of the plurality of assembly coils with respect to the pre-selected location of the cochlea;
determining a trajectory of the stimulating assembly; and
extrapolating, based on the trajectory, the relative position of the stimulating assembly with respect to the pre-selected location.

18. The method of claim 17, further comprising:
displaying, at a display screen, the shape of the stimulating assembly within the cochlea and the relative position of the stimulating assembly with respect to the pre-selected location of the cochlea.

19. The method of claim 18, wherein first, second, and third pairs of external coils are each arranged about first, second, and third axes, and further comprising:
detecting, at each of the plurality of assembly coils, magnetic fields generated by the first, second, and third pairs of external coils;
generating, at the plurality of assembly coils, three voltages based on the detected magnetic fields;
determining, based the three generated voltages generated at each of the plurality of assembly coils, an angular orientation of the corresponding assembly coil with respect to each of the first, second, and third axes; and
based on the determined angular orientations, extrapolating the shape of the stimulating assembly within the cochlea.

* * * * *